(12) United States Patent
Boufahja (10) Patent No.: US 11,798,678 B2
(45) Date of Patent: *Oct. 24, 2023

(54) SYSTEMS AND METHODS FOR DEVICE QUERY/RETRIEVE CAPABILITY DISCOVERY

(71) Applicant: GE Precision Healthcare LLC, Milwaukee, WI (US)

(72) Inventor: Abderrazek Boufahja, Strasbourg (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 193 days.

This patent is subject to a terminal disclaimer.

(21) Appl. No.: 17/446,514

(22) Filed: Aug. 31, 2021

(65) Prior Publication Data
US 2021/0391057 A1 Dec. 16, 2021

Related U.S. Application Data

(63) Continuation of application No. 16/732,656, filed on Jan. 2, 2020, now Pat. No. 11,177,033.

(51) Int. Cl.
*G16H 30/20* (2018.01)
*G06F 16/535* (2019.01)
*G06F 16/58* (2019.01)
*G06F 18/22* (2023.01)

(52) U.S. Cl.
CPC ........... *G16H 30/20* (2018.01); *G06F 16/535* (2019.01); *G06F 16/58* (2019.01); *G06F 18/22* (2023.01)

(58) Field of Classification Search
CPC ........ G06F 16/535; G06F 16/58; G06F 18/22; G16H 30/20; G16H 40/60
See application file for complete search history.

(56) References Cited

U.S. PATENT DOCUMENTS

| 5,835,735 A | 11/1998 | Mason et al. |
|---|---|---|
| 9,608,885 B2 | 3/2017 | Nolte et al. |
| 2011/0145373 A1 | 6/2011 | Awad et al. |
| 2014/0201341 A1 | 7/2014 | Nolte et al. |
| 2020/0076853 A1* | 3/2020 | Pandian ............ H04L 61/4511 |
| 2020/0160970 A1 | 5/2020 | Lyman et al. |

FOREIGN PATENT DOCUMENTS

JP  2002259242 A  9/2002

* cited by examiner

*Primary Examiner* — Manuchehr Rahmjoo
(74) *Attorney, Agent, or Firm* — McCoy Russell LLP (57) ABSTRACT

Systems and methods are provided for automatically generating a digital imaging and communications in medicine (DICOM) conformance statement. In one example, a method includes determining a set of DICOM query/retrieve capabilities of a DICOM application implemented on a DICOM device by performing a list of queries to the DICOM application, and populating a DICOM conformance statement with the determined set of DICOM query/retrieve capabilities.

18 Claims, 4 Drawing Sheets

| Level Name / Attribute Name | Tag | VR | Types of Matching |
|---|---|---|---|
| PATIENT | | | |
| PatientName | (0010,0010) | PN | U S * |
| PatientID | (0010,0020) | LO | U S * |
| IssuerOfPatientID | (0010,0021) | LO | |
| PatientBirthDate | (0010,0030) | DA | U S * R |
| STUDY | | | |
| StudyDate | (0008,0020) | DA | U S * R |
| StudyTime | (0008,0030) | TM | U S * R |
| AccessionNumber | (0008,0050) | SH | U |
| StudyID | (0020,0010) | SH | U |
| SERIES | | | |
| Modality | (0008,0060) | CS | U S * |
| SeriesNumber | (0020,0011) | IS | U S |
| SeriesInstanceUID | (0020,000E) | UI | U S L |
| StationName | (0008,1010) | SH | U S * |
| IMAGE | | | |
| InstanceNumber | (0020,0013) | IS | U S |
| SOPInstanceUID | (0008,0018) | UI | U S L |
| SOPClassUID | (0008,0016) | UI | U S L |
| ConceptNameCodeSequence | (0040,A043) | SQ | U |

FIG. 4

SYSTEMS AND METHODS FOR DEVICE QUERY/RETRIEVE CAPABILITY DISCOVERY

CROSS REFERENCE TO RELATED APPLICATIONS

The present application is a continuation of U.S. Non-Provisional patent application Ser. No. 16/732,656, entitled "SYSTEMS AND METHODS FOR DEVICE QUERY/RETRIEVE CAPABILITY DISCOVERY", and filed on Jan. 2, 2020. The entire contents of the above-listed application are hereby incorporated by reference for all purposes.

FIELD

Embodiments of the subject matter disclosed herein relate to medical imaging, and more particularly to determining capabilities of a device configured to handle medical imaging data.

BACKGROUND

Healthcare facilities often employ certain types of medical imaging modalities, such as computed tomography, magnetic resonance imaging, ultrasound imaging, and X-ray imaging. These medical imaging modalities use a common format for image data, known as digital imaging and communications in medicine (DICOM). The evolution of the DICOM format facilitated the development and expansion of picture archiving and communication systems (PACS). Use of the DICOM semantics provided by the DICOM format has become the standard method for managing imaging data access in healthcare institutions.

BRIEF DESCRIPTION

In one embodiment, a method includes determining a set of digital imaging and communications in medicine (DICOM) query/retrieve capabilities of a DICOM device by performing a list of queries to the DICOM device, and populating a machine-readable DICOM conformance statement with the determined set of DICOM query/retrieve capabilities.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of automatically generating digital imaging and communications in medicine (DICOM) conformance statements. DICOM is the common standard for medical imaging and enumerates a command set, data formats, interface specifications, communication protocols, and command syntax. DICOM sets forth information objects (types of data, such as computerized tomography, magnetic resonance, x-ray, ultrasound, etc.), service classes (actions with data, such as send, receive, print, etc.), and data transmission protocols. DICOM application services provide the ability to transfer images and image related data between DICOM applications. A DICOM service-object pair (SOP) is used to push and/or pull information between DICOM applications.

One example device that may include a DICOM application is a picture archiving and communication system (PACS). PACS have a number of roles in data management. PACS receive image data sets fed from imaging devices and manage storage systems for data persistency, managing both short-term and long-term storage. PACS accept query requests from client applications, enabling those client applications to retrieve specified data. PACS may also interface with other healthcare information systems. Various devices may communicate with a PACS via the DICOM standard, such as medical imaging devices, workstations, radiology information service (RIS) devices, etc. A device that generates, communicates, transfers, and/or stores data according to the DICOM standard may be referred to herein as a DICOM device, and may include PACS, imaging devices, RIS devices, workstations, and any other device that includes a DICOM application or is otherwise configured to handle data according to the DICOM standard.

To facilitate DICOM communication between DICOM devices, DICOM conformance statements are provided by the manufacturer of a DICOM application and/or DICOM application-implementing device. The main purpose of a DICOM conformance statement (DCS) is to describe the capabilities of the DICOM device regarding what was implemented from the DICOM standard, and what was not. This document is the main entrance for operational and integration teams of third-party devices using DICOM connectivity. The DICOM standard comprises multiple chapters, including one titled "DICOM Part2: conformance." The aim of this chapter is to structure the content of the DCS, to help connectivity providers (e.g., DICOM device manufacturers) to easily create their DCS and to help the consumer of the DICOM device to easily understand the different functions provided by the DICOM device (e.g., to enable integration of the DICOM device with other DICOM devices within a facility/enterprise). This chapter from the DICOM standard provides a general textual template that can be followed by any DICOM device, and especially a section about the DICOM devices supporting the Query/Retrieve capability. As explained above, some DICOM devices (such as PACS) retrieve and send specified data (e.g., an image set obtained on a patient) in response to a query request from a client application, thus resulting in these devices having query/retrieve capabilities (such devices may also be referred to herein as DICOM Q/R devices). The query/retrieve capabilities of a DICOM Q/R device may be set forth in the DCS, and the client application (e.g., workstation, imaging device, etc.) may be configured to send query requests according to the query/retrieve capabilities specified in the DCS for the DICOM Q/R device.

Typically, manufacturers of DICOM devices distribute their DCS in a non-formal format (PDF format for most of the encountered cases, sometimes a web site), or even fail to provide a DCS at all. As a result, integration of a new DICOM device into a larger imaging device environment (such as configuring of the connectivity to existing DICOM Q/R devices) is time consuming. The integration team (e.g., IT or other specialists who are tasked with integrating a new DICOM device into an existing system) may perform multiple actions related to the discovery of any connected DICOM Q/R devices: 1) read the DCS of the DICOM Q/R device to select the mode of integration; and 2) check that the content of the DCS is compatible with the installed tool, as the reality of the installations does not fit generally to what is declared in the official DCS. These tasks are time consuming, thus delaying DICOM device integration. Further, official DCSs are not always fully accurate, as some of the declared Query/Retrieve capabilities may be inaccurate and not supported by the DICOM Q/R device in the reality, and some of the Query/Retrieve capabilities may not be declared in the DCS, but supported by the DICOM Q/R device in reality. Thus, relying on the official DCS may result in needlessly complicated or missed Q/R functions, thus reducing efficiency in retrieving data from a DICOM Q/R device.

Thus, according to embodiments disclosed herein, the content of a DCS may be automatically generated using a model-based architecture, including an automatic fulfillment of the content populating the DCS. The model disclosed herein may generate a machine-readable DCS describing the Query/Retrieve capabilities of a connected DICOM Q/R device, such as a PACS. The disclosure provided herein includes algorithms of discovery and validation of the different components of the generated DCS. This allows the creation of a knowledge base of DICOM devices, especially on PACS provided by many multi-vendors, and to compare them based on their connection capabilities. The modelization of the content of the DCS may be based on the DICOM Part2 specification, and based also on the analysis of different DCS documents provided by multiple known DICOM Q/R devices. The automatic discovery of DICOM Q/R device capability may reduce the variable costs of a new device integration with existing applications and may also reduce the time-to-production for new devices installations.

Figure 1:
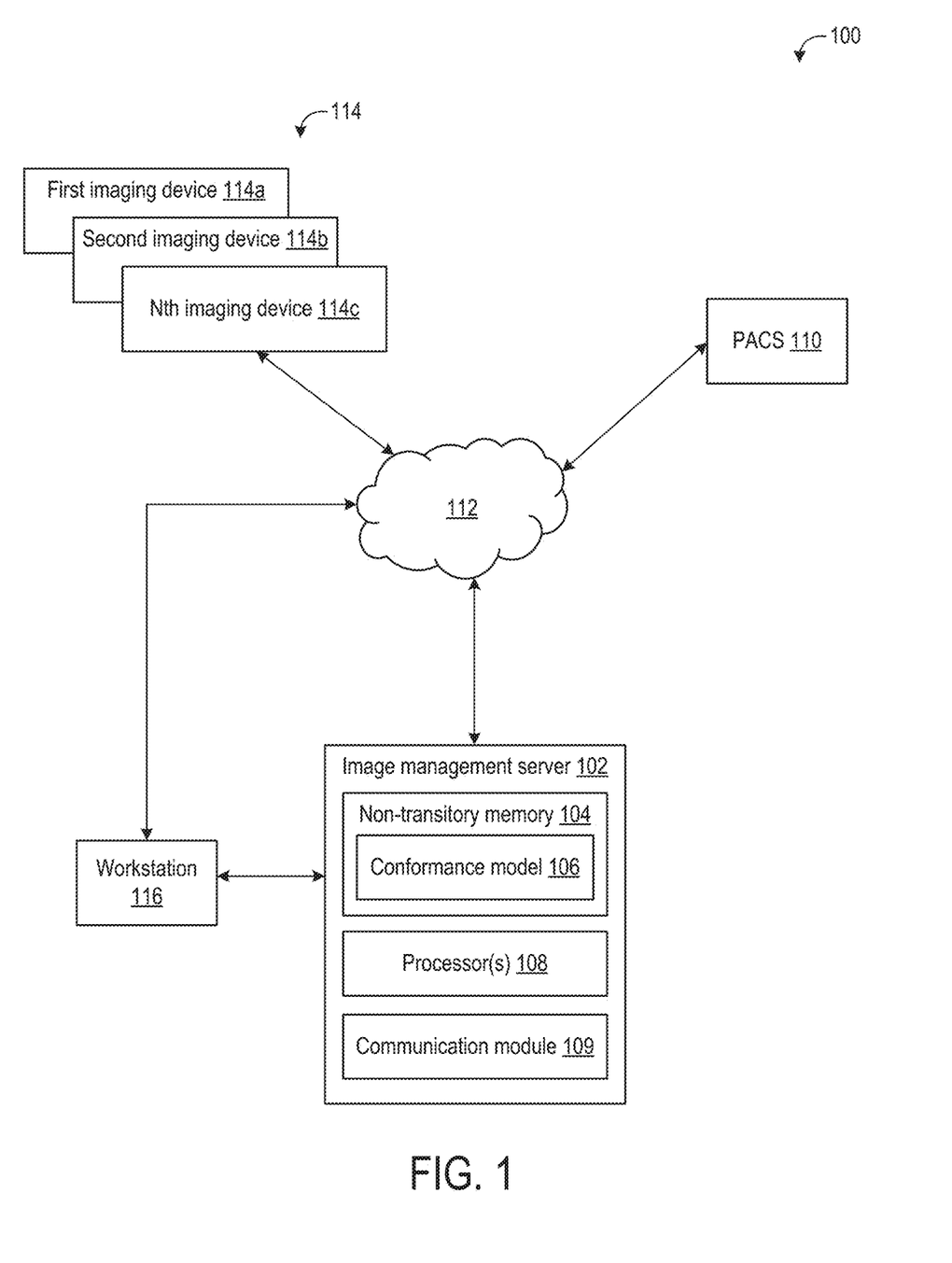
FIG. 1 schematically shows an example medical imaging system.
Figure 2:
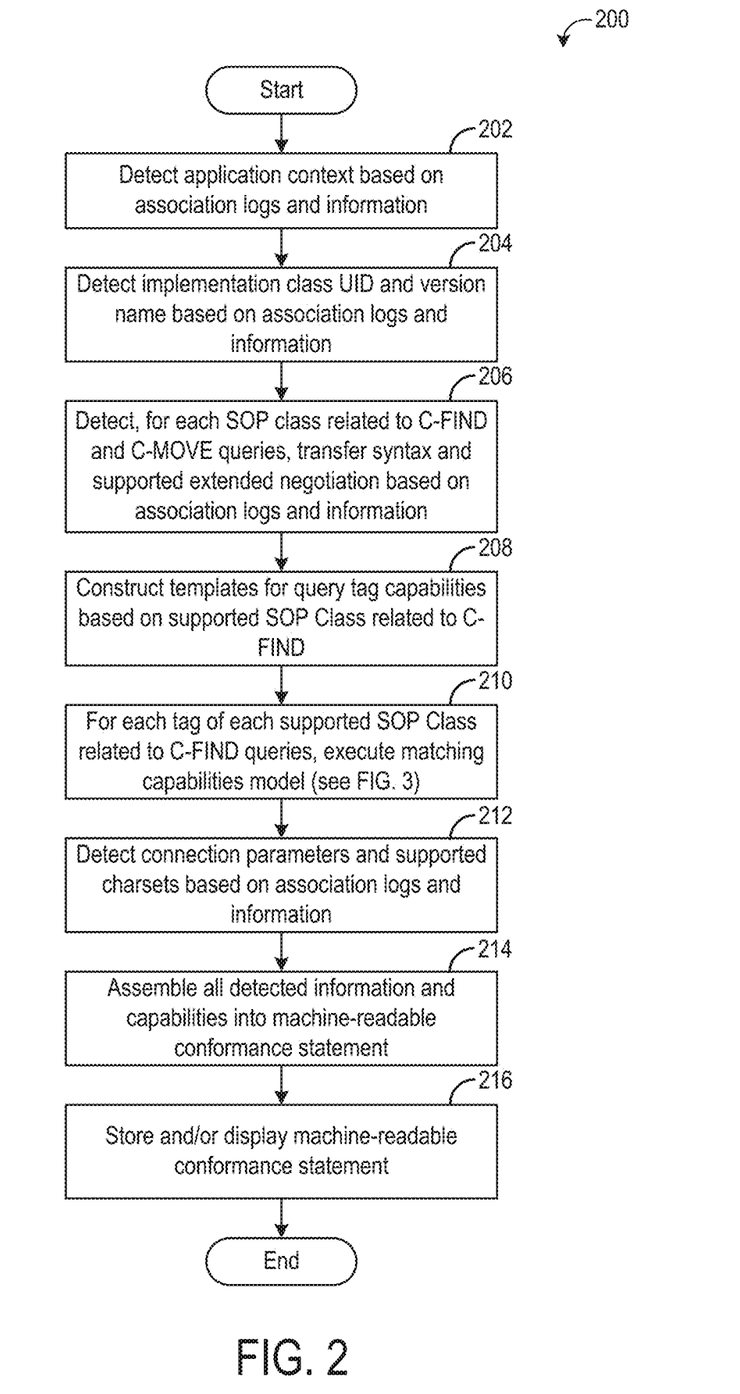
FIG. 2 is a flow chart illustrating an example method for automatically generating a DICOM conformance statement.
Figure 3:
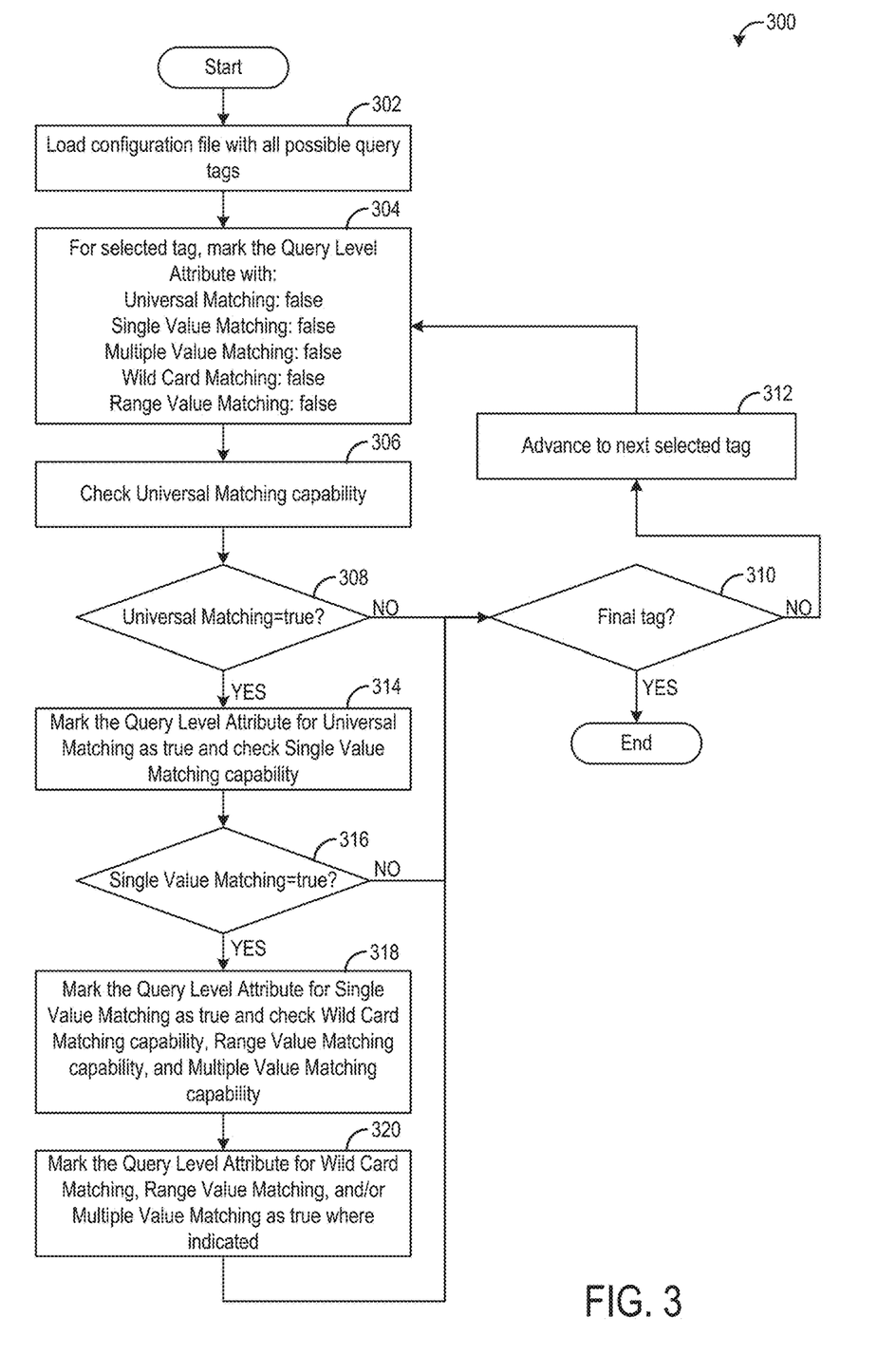
FIG. 3 is a flow chart illustrating an example method for discovering device query/retrieve capabilities for inclusion in the DICOM conformance statement generated according to the method of FIG. 2.
Figure 4:
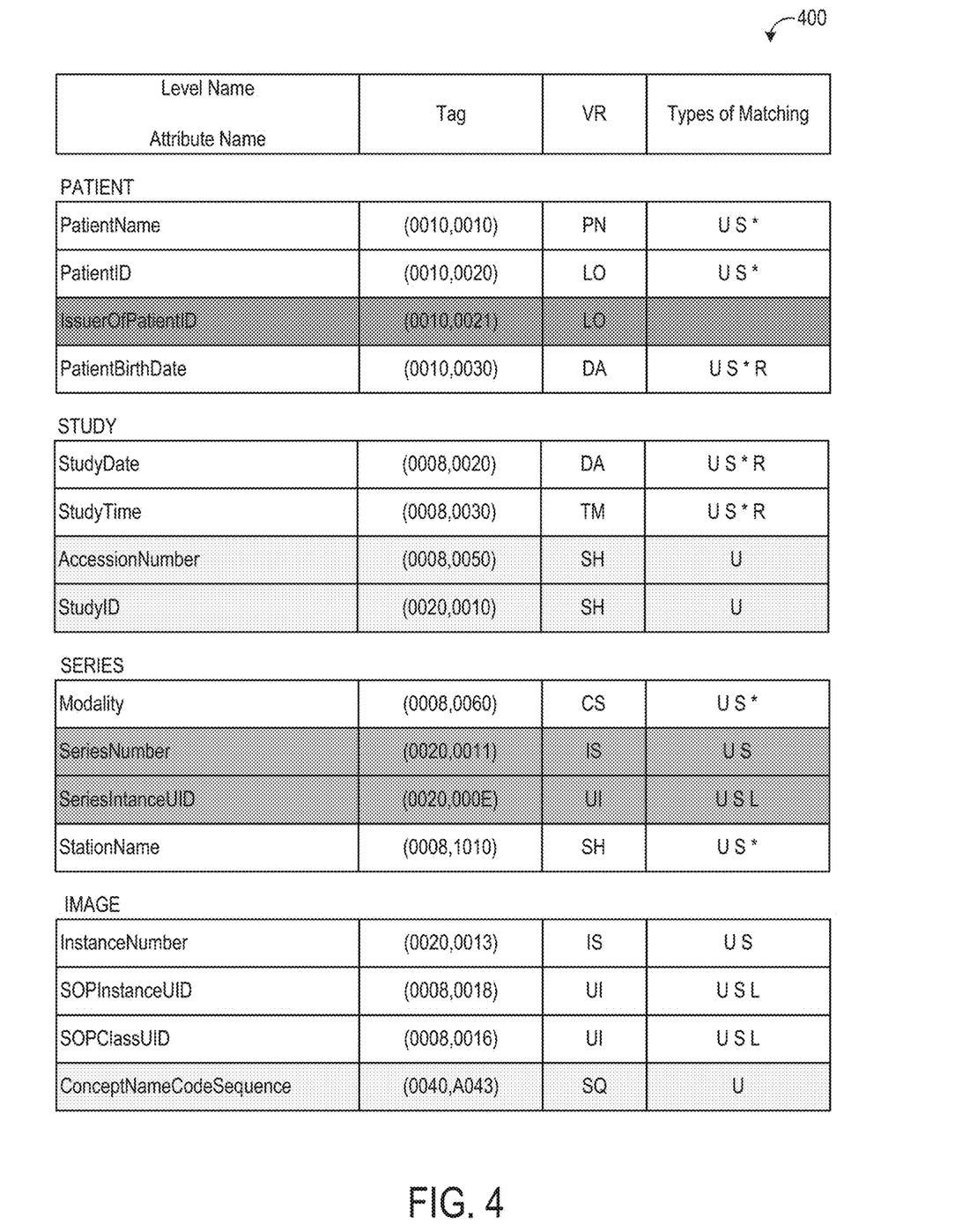
FIG. 4 shows an example DICOM conformance statement generated according to the method of FIG. 2.

FIG. 1 shows an example medical imaging environment in which the Q/R capabilities of a DICOM device may be determined in order to generate a DCS, according to the methods of FIGS. 2 and 3, which may be used to facilitate device integration. An example DCS generated according to the methods disclosed herein is shown in FIG. 4.

FIG. 1 schematically shows an example medical imaging system 100 that may be implemented in medical facility such as a hospital. Medical imaging system 100 may include a plurality of medical imaging devices 114 each communicatively coupled to a picture archiving and communication system (PACS) 110. The plurality of medical imaging devices 114 includes a first imaging device 114a, a second imaging device 114b, and on up to an Nth imaging device 114c. The plurality of medical imaging devices 114 may include, as non-limiting examples, magnetic resonance imaging (MM) devices, computed tomography (CT) devices, positron emission tomography (PET) devices, X-ray devices (including digital mammography devices, fluoroscopy devices, interventional devices, etc.), ultrasound devices, single-photon emission computerized tomography (SPECT) devices, and/or combinations thereof. As a non-limiting example, first imaging device 114a may be a CT device and second imaging device 114b may be an X-ray device.

Each medical imaging device may be configured to acquire medical images of a patient and send the acquired images to PACS 110 for long-term storage. PACS 110 may store the images and, when requested, may retrieve one or more images and send the retrieved images to one or more connected devices (as explained in more detail below).

Medical imaging system 100 further includes an image management server 102. Server 102 may include resources (e.g., memory 104, processor(s) 108) that may be allocated to store and execute a conformance model 106 configured to discover query/retrieve capabilities of a connected DICOM devices, such as PACS 110, and populate a machine-readable DICOM conformance statement with the discovered capabilities. Once an automatically-generated DICOM conformance statement is generated for a particular device (e.g., for PACS 110), server 102 may be configured to query the device according to the capabilities set forth in the DICOM conformance statement, when requested by a user.

Server 102 includes a communication module 109, memory 104, and processor(s) 108 to store and execute the conformance model 106, as well as send and receive communications, graphical user interfaces, medical data, and other information. In one non-limiting example, server 102 may be configured to determine patient radiation dosage information based on information received from PACS 110 (e.g., patient images, imaging workflow/protocols, etc.) and output a graphical user interface (e.g., to workstation 116 and/or another display device, such as a display device associated with one of the plurality of imaging devices 114) including the patient dosage information.

Communication module 109 facilitates transmission of electronic data within and/or among one or more systems. Communication via communication module 109 can be implemented using one or more protocols. In some examples, communication via communication module 109 occurs according to one or more standards (e.g., Digital Imaging and Communications in Medicine (DICOM), Health Level Seven (HL7), ANSI X12N, etc.). Communication module 109 can be a wired interface (e.g., a data bus, a Universal Serial Bus (USB) connection, etc.) and/or a wireless interface (e.g., radio frequency, infrared, near field communication (NFC), etc.). For example, communication module 109 may communicate via wired local area network (LAN), wireless LAN, wide area network (WAN), etc. using any past, present, or future communication protocol (e.g., BLUETOOTH™, USB 2.0, USB 3.0, etc.).

Memory 104 one or more data storage structures, such as optical memory devices, magnetic memory devices, or solid-state memory devices, for storing programs and routines executed by processor(s) 108 to carry out various functionalities disclosed herein. Memory 104 may include any desired type of volatile and/or non-volatile memory such as, for example, static random access memory (SRAM), dynamic random access memory (DRAM), flash memory, read-only memory (ROM), etc. Processor(s) 108 may be any suitable processor, processing unit, or microprocessor, for example. Processor(s) 108 may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, server 102 and PACS 110 are shown in FIG. 1 as each constituting a single entity, but it is to be understood that server 102 and/or PACS 110 may be distributed across multiple devices, such as across multiple servers.

As shown in FIG. 1, a workstation 116 is shown communicatively coupled to server 102. Additional workstations may be present in medical imaging system 100, such as workstations associated with PACS 110 and/or one or more of the plurality of imaging devices 114. Each workstation may include a processor, memory, communication module, user input device, display (e.g., screen or monitor), and/or other subsystems and may be in the form of a desktop computing device, a laptop computing device, a tablet, a smart phone, or other device.

While not specifically shown in FIG. 1, additional devices described herein (the plurality of imaging device 114, PACS 110, workstation 116) may likewise include user input devices, memory, processors, and communication modules/interfaces similar to communication module 109, memory 104, and processor(s) 108 described above, and thus the description of communication module 109, memory 104, and processor(s) 108 likewise applies to the other devices described herein. The user input devices may include keyboards, mice, touch screens, microphones, or other suitable devices.

Conformance model 106 may automatically generate a DCS for PACS 110 describing the query/retrieve (Q/R) capabilities of PACS 110. The DCS generated by the conformance model 106 may be machine- and/or human-readable and may be stored in memory 104. Further, in some examples, the DCS generated by conformance model 106 may be shared with other DICOM devices that communicate with PACS 110 (e.g., one or more of the plurality of imaging devices 114, workstations, etc.) via direct communication or via storage of the DCS in a common storage location accessible by the other DICOM devices. Further still, conformance model 106 may generate a DCS for one or more additional DICOM devices, such as a RIS (not shown in FIG. 1), additional PACS (e.g., located at different facilities), etc.

As explained above, server 102 may be configured to determine radiation dose information for one or more patients. To determine the radiation dose information, server 102 may be configured to retrieve various information from PACS 110, such as images of a patient obtained with a CT device (e.g., the first imaging device 114a), CT device settings used to obtain the images, etc. Once the DCS for PACS 110 has been generated by conformance model 106, the DCS may be used to set query/retrieve settings for server 102, which may enable server 102 to efficiently ask for and receive the information from PACS 110 in order to determine the radiation dose information.

While conformance model 106 is shown in FIG. 1 as being stored and executed on server 102, it is to be understood that other DICOM devices in medical imaging system 100 may include a similar conformance model. For example, one or more of the plurality of imaging devices 114 may store and execute a conformance model, PACS 110 may store and execute a conformance model, etc.

FIG. 2 is a flow chart illustrating a method 200 for automatically generating a DICOM conformance statement for a DICOM application executing on a DICOM device, such as a PACS. Method 200 may be implemented on a computing device in communication with a DICOM device, such as server 102 in communication with PACS 110. Method 200 may be executed by a processor of the computing device (such as processor(s) 108 of server 102 of FIG. 1) according to instructions stored on a non-transitory memory of the device (e.g., memory 104 shown in FIG. 1).

At 202, an application context of the DICOM application is detected based on association logs and information from the DICOM application. For example, when the DICOM device and the computing device implementing method 200 first communicate (e.g., set up an association), the DICOM device may send an association log that includes, among other information, the application context of the DICOM application, which may include the specification of the type of communication used between the DICOM application and other application entities (e.g., the computing device executing method 200). The application context may be detected in the response of the DICOM association. For example, an association with the DICOM device may be opened, according to the A-Associate-AC Protocol Data Unit (PDU) or application context packet, and the application context field may be gathered.

At 204, the DICOM application implementation class unique identifier (UID) and implementation version name are detected based on the association logs and information. The implementation class UID may uniquely identify a specific class of implementation of the DICOM application, and the implementation version name may provide a mechanism to distinguish between two versions of the same implementation. For example, an association with the DICOM device is opened, according to the A-Associate-AC PDU, and the fields Implementation Class UID and Implementation version name are gathered from the A-Associate-AC PDU or the A-Associate-RQ PDU.

At 206, a transfer syntax and supported extended negotiation are determined for each service-object pair (SOP) class related to C-FIND and C-MOVE queries based on the association logs and information. Transfer syntax may include the encoding used (e.g., by the DICOM device) for exchange of DICOM information objects and messages. An SOP class may include a specification of the network or media transfer of a particular type of data (e.g., object). The SOP classes related to C-FIND and C-MOVE may include Patient Root Query/Retrieve Information Model and Study Root Query/Retrieve Information Model.

At 208, templates for the SOP class tag queries are constructed based on the supported SOP classes related to C-FIND. For example, for each supported SOP class, a list of queries may be assembled that will be used to determine the Q/R capabilities of the DICOM application. For each Root Model (patient or study), there may be different levels (referred to as query level class) for querying the DICOM application, such as Patient, Study, Series, and Image. For the Patient Root Model, the levels may be Patient, Study, Series, and Image, while for the Study Root Model, the levels may Study, Series, and Image. The query level class refers to the list of tags supported for query. Each tag (also referred to as query level attribute) indicates an attribute that may be queried, such as study date, study time, accession number, patient ID, patient name, etc. Each tag may be a 32-bit identifier for a data element, represented as a pair of four digit hexadecimal numbers, the group and the element. Odd group numbers may refer to private (e.g., manufacturer-specific) data elements. The Q/R capabilities of the DICOM application may be determined by determining the matching capability of each tag, as explained below.

The templates may be predefined templates that are extensible, based on the need of the consuming application (e.g., the DICOM application that will be implemented on the device implementing method 200). The matching tags related to the Patient, Study, and Series level are defined by DICOM standard. However, the Image level is specific for each image. Some of the tags are common to all the images, and these common tags are defined by default in the templates. In the example presented herein where the image management server 102 (executing method 200 via the conformance model 106) is configured to determine patient radiation dosage information based on information received from PACS 110, the tags needed for radiation dose recording (RDSR) tracking are also defined in the templates. However if a consuming application of the generated DCS needs to test extra tags, the application is configurable for such use cases.

The predefined template assumes that all the tags are supported for querying, and includes a predefined list of attributes to be tested (which may not include all possible attributes, as explained below). In this way, the predefined template is an empty template where there are no association information defined, but only the list of the attributes/tags that need to be tested for Patient Root level and for Study Root level. The list of supported SOP Classes is a fixed enumeration: the list of SOP Classes defined by DICOM for Q/R from a device. The list of attributes/tags may be an XML file configured with the most used tags, as defined by DICOM.

At 210, a matching capabilities model is executed in order to determine the matching capabilities for each tag of each supported SOP class. Additional details regarding the matching capabilities model will be described below with respect to FIG. 3. Briefly, the matching capabilities model may send a list of queries to the DICOM application in order to determine whether matching is supported for each tag of each SOP class, and if so, what type of matching. The different types of matching include universal matching, single value matching, wild card matching, multiple value matching, and range value matching. Based on the responses to the list of queries from the DICOM application, the matching capabilities of the DICOM application, for each supported tag, may be determined.

At 212, connection parameters and supported character sets (charsets) for the DICOM application are detected based on the association logs and information. The connection parameters may include the IP address of the DICOM device hosting the DICOM application, the port number of the DICOM application, PDU size, etc. The supported charsets may include the character sets (e.g., Latin alphabets, Arabic, Greek, etc.) supported by the DICOM application.

At 214, the detected information and matching capabilities are assembled into a machine-readable conformance statement. For example, the detected application context, implementation class UID, implementation version name, transfer syntax/supported extended negotiation, connection parameters, and supported charsets may all be populated in the conformance statement. Further, for each tag of each supported SOP class, the determined matching capabilities may be populated in the conformance statement. For example, for the tag "PatientName" of the Patient Root Model, the determined matching capabilities for "PatientName" may be entered into the conformance statement, where the matching capabilities include an indication of whether universal matching, single value matching, wildcard matching, multiple value matching, and/or range value matching are supported. The conformance statement may be generated in a suitable machine-readable format, such as XML.

At 216, the conformance statement may be stored and/or displayed on a display device operably coupled to the computing device, such as a display device of workstation 116. The conformance statement may be stored in memory of the computing device (e.g., memory 104) and/or another storage location, such as a common database where other DICOM devices can access the conformance statement. In some examples, the information included in the conformance statement (e.g., the Q/R capabilities) may be used as input for another DICOM application, which may read the conformance statement and create intelligent queries for the DICOM application in order to index the content of the DICOM application. Method 200 then ends.

FIG. 3 is a flow chart illustrating a method 300 for discovering the query/retrieve capabilities of a DICOM application implemented on a DICOM device, such as a PACS, during the generation of a DICOM conformance statement for the DICOM application. Method 300 may be implemented on a computing device in communication with a DICOM device, such as server 102 in communication with PACS 110. Method 300 may be executed by a processor of the computing device (such as processor(s) 108 of server 102 of FIG. 1) according to instructions stored on a non-transitory memory of the device (e.g., memory 104 shown in FIG. 1). In some examples, method 300 may be carried out as part of method 200, e.g., method 300 may be carried out at 210 of method 200.

At 302, a configuration is file loaded that includes all possible query tags for determining the Q/R capabilities of the DICOM application. The possible query tags may be assembled based on the DICOM standard, an analysis of existing DICOM conformance statements, and/or based on the information obtained while executing method 200 (e.g., supported SOP classes). As explained above, the query tags may each indicate an attribute that may be queried, such as study date, study time, accession number, patient ID, patient name, etc., and each tag may be a 32-bit identifier for a data element.

At 304, for a selected tag (e.g., a first tag from the possible query tags), the Query Level Attribute for that tag may be marked so that each matching attribute (that will be tested as described below) is initially indicated as being false (e.g., not having that matching attribute). Thus, for the selected tag, universal matching is marked as false, single value matching is marked as false, multiple value matching is marked as false, wild card matching is marked as false, and range value matching is marked as false. In this way, the default matching capabilities for the selected tag may be false (e.g., not supported) and as each matching capability is tested, if that capability is supported, the capability may be adjusted to true (e.g., supported), as explained below.

At 306, the universal matching capability of the selected tag is checked. To check the universal matching capability, a list of patient IDs associated with exams stored on the DICOM device is assembled. For example, one or more exams/studies currently stored on the DICOM device may be accessed/determined, and a corresponding patient ID for each of the one or more exams is determined and added to the list. The level of the selected tag is also determined, based on the selected tag (e.g., is the selected tag Patient level, Study level, Series level, or Image level). Then, for each patient ID on the list, a universal matching query is sent to the DICOM application. Each universal matching query may include the selected tag in a return key of that universal matching query. In this way, the universal matching query may include a request, from the device implementing method 300 (e.g., implementing the conformance model), for the DICOM application to perform a match of a patient ID (known to be stored on the DICOM device) and for the DICOM application to return value(s) for the selected tag associated with the patient ID. As an example, if the selected tag is PatientName, the universal matching query may include a query to find a selected patient ID and return the patient name associated with that patient ID. In this way, the input for the matching capabilities model is a list of Patient IDs identified in the DICOM device. This list of patient IDs may be manually provided or detected by performing some C-FIND on the StudyDate on the DICOM device. Once the list of patient IDs is generated, for each tag on the configuration file, a universal matching check is performed on the selected tag for all the patient IDs (e.g., one query per patient ID).

In some examples, additional information may be needed to perform the universal matching query. For example, in hierarchical DICOM applications, higher level entities must be identified before matching attributes of a lower level entity. As an example, if the selected tag is SeriesNumber, the StudyInstanceUID for each patient ID may be determined prior to performing the universal matching queries for the series number, as the study instance UID is required to perform queries of any series level tags.

The response(s) to the one or more universal matching queries may be analyzed to determine if universal matching is supported for the selected tag. For example, if at least one response from the DICOM application to a universal matching query includes a return value for the selected tag, then it may be determined that the DICOM application supports universal matching for the selected tag. However, if each response from the DICOM application to each universal matching query does not include a return value for the selected tag, then it may be determined that the DICOM application does not support universal matching for the selected tag. Thus, if the selected tag is not provided in the DICOM studies related to a patient, even if it is queried as a return key, the selected tag is not provided by the DICOM application, thus if at least one of the patients have the selected tag in a corresponding exams, it is automatically determined that the selected tag is part of the supported return keys.

At 308, method 300 determines if universal matching is supported for the selected tag (e.g., Universal Matching=true?). If universal matching is not supported (e.g., the responses to the universal matching queries did not include return values for the selected tag), the selected tag is not supported for querying of any kind (e.g., all the matching attributes for the selected tag remain as false) and method 300 proceeds to 310 to determine if the selected tag is the final tag to be queried. If the selected tag is the final tag to be queried (e.g., all the possible tags as defined in the template have been queried), method 300 ends. If the selected tag is not the final tag, method 300 proceeds to 312 to advance to the next selected tag, and then method 300 proceeds to 304 to repeat the process of testing the matching capabilities for the next selected tag.

Returning to 308, if universal matching is supported for the selected tag, method 300 proceeds to 314 to mark the Query Level Attribute for Universal Matching for the selected tag as true and check Single Value Matching capability for the selected tag. In order to check single value matching capabilities for the selected tag, two tests are performed, a pass test and a fail test, using the responses from the universal matching queries. As explained above, the universal matching queries performed at 306 result in the reception of responses to the universal matching queries from the DICOM application that include return values (e.g., the values requested in the return keys for the universal matching queries), which indicate real values for the selected tag (e.g., real patient names, real series numbers, real study dates, etc., dependent on the selected tag being queried). These return values obtained from the universal matching queries are then used to test the single value matching capabilities.

The pass test includes performing, for each response to each universal matching query, a first single value query for the selected tag using a respective returned value from that response. For example, the return value from one of the universal matching queries (e.g., a specific patient name) may be used as the matching key for a first single value query in addenda to the needed query level identifiers of the selected tag. If the DICOM application responses match the query parameters (e.g., the DICOM application returns one or multiple matches with the selected query parameters), a check is performed to confirm that all the found matchings are related to the selected tag value, and the pass test is deemed to have returned expected results if the check passes. If the DICOM application responses do not match the query parameters (e.g., the DICOM application does not return the requested DICOM objects), the pass test is deemed to not have returned expected results.

The fail test includes performing, for each response to each universal matching query, a second single value query for the selected tag using a different value than the respective returned value from that response and including the needed query level identifiers of the selected tag. In the query, the identifiers are kept, for example if the selected tag is SeriesNumber, for a hierarchical PACS, the PatientID and the StudyInstanceUID are needed, in order to perform the query. A virtual or purposely erroneous return value that does not match any of the return values from the universal matching queries (e.g., a made-up patient name) may be used as the matching key for a second single value query. If the DICOM application responses do not include the original return value (e.g., the value of the selected tag found in the return key, in the universal matching testing), the fail test is deemed to have returned expected results. If the DICOM application responses do include the original return value, the fail test is deemed to not have returned expected results.

As an example, a universal matching test for a patient having PatientID 1.1 may be performed on the selected tag of PatientName. The request may include Query Level: Patient and Query Tags: [PatientID] 1.1; [Patient Name] - - - (empty). The response from the DICOM application may include Query Level: Patient and Response Tags: [PatientID] 1.1; [PatientName] Moore. Thus, the universal matching query response return value includes a specific name, Moore.

The pass test for the single value matching may include a request with Query Level: Patient and Query Tags: [PatientID] 1.1; [PatientName] Moore, thereby using the return value from the universal matching query response. If the response to the single value matching pass test query includes Query Level: Patient and Response Tags: [PatientID] 1.1; [PatientName] Moore, the pass test passes. If the response contains the Tag PatientName !=Moore, the pass test fails, and thus single value matching is not supported.

The fail test for the single value matching may include a request for Query Level: Patient and Query Tags: [PatientID] 1.1; [PatientName] John. If the response is "No found patient," the fail test may pass. If the response is Query Level: Patient and Response Tags: [PatientId] 1.1; [PatientName] Moore, the fail test failed because the response on the PatientName is equal to the original tested value, which is "Moore".

If both the pass test and the fail test return expected results, the DICOM application is determined to support single value matching for the selected tag. If either or both of the pass test and the fail test do not return expected results, the DICOM application is determined not to support single value matching for the selected tag.

At 316, method 300 determines if single value matching is supported for the selected tag (e.g., Single Value Matching=true?). If single value matching is not supported, the remaining matching capabilities cannot be supported, and thus the querying of the matching capabilities for the selected tag are complete and method 300 proceeds to 310 to determine if the selected tag is the final tag to be queried. If the selected tag is the final tag to be queried (e.g., all the possible tags have been queried), method 300 ends. If the selected tag is not the final tag, method 300 proceeds to 312 to advance to the next selected tag, and then method 300 proceeds to 304 to repeat the process of testing the matching capabilities for the next selected tag.

If single value matching is supported for the selected tag, method 300 proceeds to 318 to mark the Query Level Attribute for Single Value Matching for the selected tag as true and check Wild Card Matching capability, Range Value Matching capability, and Multiple Value Matching for the selected tag.

To check wild card matching capability for the selected tag, one or more wild card queries are performed. The wild card queries may include, for each return value from each response to each universal matching query, transforming the last character of the returned value for that response to a wild card and performing a wild card query with the transformed returned value. For example, if the return value for a universal matching query is a specific patient name (e.g., John Doe), the last character (e.g., the letter e) is transformed to a wild card (e.g., an asterisk) character and the transformed return value (e.g., John Do*) is used as the matching key for the wild card query. If each wild card query returns expected results, it is determined that the DICOM application supports wild card matching. The expected results include the responses to the query all having the string John Do and the responses including the original return value that was transformed (e.g., the responses should include John Doe).

Range value matching may only be tested on date and time tags, such as StudyDate, SeriesDate, SeriesTime, etc. To check range value matching, a DICOM reference object is selected based on each response to each universal matching query, and the returned value of the selected tag for the DICOM reference object is identified (e.g., a study date is identified based on the universal matching query responses, where the study date is confirmed to be associated with a study stored on the DICOM device). Two queries are then performed, a first range value query using a first range that spans the identified returned value of the selected tag for the DICOM reference object (e.g., a date range that spans the identified study date) and a second range value query using a second range that does not span the identified returned value of the selected tag for the DICOM reference object (e.g., a date range that does not span the identified study date). The expected results for the first query include the DICOM reference object being returned; if any other objects are returned, those objects should also have a value that falls within the first range. For example, if the DICOM reference object is a study performed on Jan. 1, 2019, the first query may include "return all studies between Jan. 1, 2019-Feb. 1, 2019," and the response to the query should include the study performed on Jan. 1, 2019. Any other studies returned should have been performed between Jan. 1, 2019-Feb. 1, 2019. The expected results for the second query include the DICOM reference object not being returned. If both the first range value query and the second range value query return expected results, it is determined that the DICOM application supports range value matching.

Multiple value matching may only be tested on tags supporting multiple values, such as ModalitiesInStudy, SOPInstanceUID, etc. To check multiple value matching, a DICOM reference object is selected based on each response to each universal matching query, and the returned value of the selected tag for the DICOM reference object is identified (e.g., a study is identified based on the universal matching query responses, where the modalities in the study are identified). Three tests/queries are then performed. A first multiple value query is performed using the returned value of the selected tag for the DICOM reference object and a virtual value, in a first order. For example, the first multiple value query may include a request to return all studies including an identified modality (e.g., CT) and a second modality (which may be fictitious or least not match the modalities in the selected study). Expected results from the first multiple value query include the DICOM reference object being returned. A second multiple value query is performed using the returned value of the selected tag for the DICOM reference object and the virtual value, in a reversed order relative to the first order (e.g., the second multiple value query may include a request to return all studies including the second modality and the identified modality). Expected results from the second multiple value query include the DICOM reference object being returned. A third multiple value query is performed using two virtual values (e.g., the second modality and a third modality which may also be fictitious or at least not match the modalities in the selected study). Expected results from the third multiple value query include the DICOM reference object not being returned. If the first multiple value query, the second multiple value query, and the third multiple value query each return expected results, it may be determined that the DICOM application supports multiple value matching.

At 320, the Query Level Attribute for Wild Card Matching, Range Value Matching, and/or Multiple Value Matching for the selected tag may be marked as true where indicated. For example, if the wild card matching test indicates that wild card matching for the selected tag is supported, the Wild Card Matching Query Level Attribute is marked as true. If the range value matching test indicates that range value matching is supported for the selected tag, the Range Value Matching Query Level Attribute is marked as true. If the multiple value matching test indicates that multiple value matching for the selected tag is supported, the Multiple Value Matching Query Level Attribute is marked as true. Method 300 then proceeds to 310, as explained above.

Each time a selected tag is queried according to method 300, the matching capabilities for that tag are determined and then saved in the Query Level Attribute for that tag. The matching capabilities for each tag are determined and then the determined matching capabilities are populated in the conformance statement as explained at 214 of method 200.

FIG. 4 shows an example DICOM conformance statement (DCS) 400 for a patient root Q/R information model for a given DICOM application (e.g., implemented on PACS 110) that may be generated according to the methods of FIGS. 2 and 3 described above. DCS 400 may be in a format suitable for display on a display device. DCS 400 includes an attribute name, tag, value representation (VR), and types of matching supported for each query level attribute/tag. The attributes are organized by level. For example, as shown, the Patient level includes PatientName, PatientID, IssuerOfPatient ID, and PatientBirthDate; the Study level includes StudyDate, StudyTime, AccessionNumber, and StudyID; the SeriesLevel includes Modality, SeriesNumber, SeriesInstanceUID, and StationName; the Image level includes InstanceNumber, SOPInstanceUID, SOPClassUID, and ConceptNameCodeSequence. The VR describes the data type and format of each attribute. Example VRs shown in FIG. 4 include patient name (PN), long string (LO), date (DA), time (TM), short string (SH), code string (CS), integer string (IS), unique identifier (UI), and sequence of items (SQ). The types of matching are the matching capabilities determined according to the method of FIG. 3. In the example shown, U stands for universal matching, S stands for single value matching, * stands for wild card matching, R stands for range value matching, and L stands for multiple value matching.

As an example, the attribute PatientName has a tag of (0010,0010) and a VR of PN. As determined by the conformance model, the types of matching that can be performed for PatientName include universal, single value, and wild card; range value and multiple value are not supported. For PatientID, supported matching includes universal, single value, and wild card. However, for IssueOfPatientID, matching is not supported. It is to be understood that the attributes and matching capabilities shown in FIG. 4 are non-limiting and that a DCS generated according to methods 200 and 300 may include more or fewer attributes/tags and that the DCS may take on different visual appearance without departing from the scope of this disclosure.

DCS 400 may include color coding to quickly notify a user of the matching capabilities for a given tag. For example, the color coding may include unsupported tags (e.g., IssuerOfPatientID) marked in red, tags supported for at least universal, single value, and wild card matching marked in green (e.g., PatienName), tags where only universal matching is supported (e.g., AccessionNumber) marked in orange, and tags where universal and single value are supported (and where applicable, range and multiple value) but not wild card (e.g., SeriesNumber) marked in yellow, although other colors may be used without departing from the scope of this disclosure.

The tags that may be queried herein for matching capability determination and inclusion in a DCS include two types of tags: common and advanced. The common tags may include tags which are commonly exposed by DICOM applications (such as DICOM applications implemented on a PACS), such as the IssuerOfPatientId, the StationName, etc. The advanced tags may be tags which are not common to be exposed by all PACS, such as PatientBirthTime. If the tag is common, even if it is not supported, it may be shown on the DCS as a red tag. However, if the tag is advanced and not supported, that tag may not be shown on the DCS, as there may be a relatively high number of advanced tags, and showing the unsupported advanced tags in the DCS is generally not relevant for the user and may swamp the DCS without added value.

DCS 400 is shown in a format suitable for display on a display device, and this format may or may not be machine-readable. As explained above, the aromatically generated DCSs described herein may be generated in a machine-readable format which may facilitate automatic integration of devices and/or sharing of the DCS among devices. The machine-readable DCS may be in XML. An example XML, description of the matching capability for a given DICOM application (e.g., PACS 110) for the patient birth date attribute is shown below.

```
<listQueryLevelAttributesqueryTag="PatientBirthDate" optionality="O"
advanced="true">
    <attributeMatching>
        <singleValueMatching>true</singleValueMatching>
        <multipleValuesMatching>false</multipleValuesMatching>
        <universalMatching>true</universalMatching>
        <wildCardMatching>true</wildCardMatching>
        <rangeMatching>true</rangeMatching>
    </attributeMatching>
</listQueryLevelAttributes>
```

Thus, the conformance model described herein may determine that the attribute patient birth date is supported for querying with the matching capabilities of universal, single value, wild card, and range value, but not multiple value.

The technical effect of automatically discovering query/retrieve capabilities of a DICOM device and generating a DICOM conformance statement including the discovered query/retrieve capabilities is that the DICOM device may be automatically integrated into an existing imaging environment, expediting device integration and lowering integration and deployment costs. The automatic Q/R capabilities discovery and DCS generation described herein may be performed to discover Q/R capabilities of any DICOM application manufactured by any manufacturer, which may facilitate rapid device integration regardless of the set-up of the existing imaging environment.

An embodiment of a method includes determining a set of digital imaging and communications in medicine (DICOM) query/retrieve capabilities of a DICOM application implemented on a DICOM device by performing a list of queries to the DICOM application; and populating a DICOM conformance statement with the determined set of DICOM query/retrieve capabilities. In a first example of the method, determining the set of DICOM query/retrieve capabilities comprises identifying one or more supported service object pair (SOP) classes related to query/retrieve, and for each supported SOP class, identifying one or more tags of that SOP class. In a second example of the method, which optionally includes the first example, determining the set of DICOM query/retrieve capabilities comprises determining a respective query level and matching capabilities for each tag of each supported SOP class. In a third example of the method, which optionally includes one or both of the first and second examples, the matching capabilities comprise whether or not the DICOM application supports universal matching, single value matching, multiple value matching, wild card matching, and/or range value matching. In a fourth example of the method, which optionally includes one or more or each of the first through third examples, determining universal matching capabilities for a selected tag by performing a list of queries to the DICOM application comprises: assembling a list of patient IDs associated with exams stored on the DICOM device; for each patient ID on the list, sending a universal matching query to the DICOM application, each universal matching query including the selected tag in a return key; if at least one response from the DICOM device to a universal matching query includes a return value for the selected tag, indicating that the DICOM application supports universal matching for the selected tag; and if each response from the DICOM application to each universal matching query does not include a return value for the selected tag, indicating that the DICOM device does not support universal matching. In a fifth example of the method, which optionally includes one or more or each of the first through fourth examples, determining single value matching capabilities for the selected tag by performing a list of queries to the DICOM application comprises: performing a pass test that includes, for each response to each universal matching query, a first single value query for the selected tag using a respective return value from that response; performing a fail test that includes, for each response to each universal matching query, a second single value query for the selected tag using a different value than the respective return value from that response; and if both the pass test and the fail test return expected results, indicating that the DICOM application supports single value matching for the selected tag. In a sixth example of the method, which optionally includes one or more or each of the first through fifth examples, determining wild card matching capabilities for the selected tag by performing a list of queries to the DICOM application comprises: for each return value from each response to each universal matching query, transforming the last character of the return value for that response to a wild card and performing a wild card query with the transformed return value; and if each wild card query returns expected results, indicating that the DICOM application supports wild card matching. In a seventh example of the method, which optionally includes one or more or each of the first through sixth examples, determining range value matching capabilities for the selected tag comprises: selecting a DICOM reference object based on each response to each universal matching query, and identifying the return value of the selected tag for the DICOM reference object; performing a first range value query using a first range that spans the return value of the selected tag for the DICOM reference object; performing a second range value query using a second range that does not span the return value of the selected tag for the DICOM reference object; and if both the first range value query and the second range value query return expected results, indicating that the DICOM application supports range value matching. In an eighth example of the method, which optionally includes one or more or each of the first through seventh examples, determining multiple value matching capabilities for the selected tag comprises: selecting a DICOM reference object based on each response to each universal matching query, and identifying the return value of the selected tag for the DICOM reference object; performing a first multiple value query using the return value of the selected tag for the DICOM reference object and a virtual value, in a first order; performing a second multiple value query using the return value of the selected tag for the DICOM reference object and the virtual value, in a reversed order relative to the first order; performing a third multiple value query using two virtual values; and if the first multiple value query, the second multiple value query, and the third multiple value query each return expected results, indicating that the DICOM application supports multiple value matching. In a ninth example of the method, which optionally includes one or more or each of the first through eighth examples, the method further includes outputting the DICOM conformance statement for display on a display device. In a tenth example of the method, which optionally includes one or more or each of the first through ninth examples, populating the DICOM conformance statement with the determined set of DICOM query/retrieve capabilities comprises populating a machine-readable DICOM conformance statement with the determined set of DICOM query/retrieve capabilities.

An embodiment of a system includes a computing device communicatively coupled to a DICOM device and storing instructions executable to: determine a set of DICOM query/retrieve capabilities of the DICOM device by performing a list of queries to the DICOM device; populate a machine-readable DICOM conformance statement (DCS) with the determined set of DICOM query/retrieve capabilities; and output a representation of the DCS for display on a display device. In a first example of the system, the instructions are further executable to automatically integrate the DICOM device according to the DCS. In a second example of the system, which optionally includes the first example, the DICOM device implements a DICOM application configured to retrieve and send data according to a DICOM standard. In a third example of the system, which optionally includes one or both of the first and second examples, the DICOM device is a picture archiving and communication system.

An embodiment of a method for a computing device includes obtaining, via the computing device, a set of digital imaging and communications in medicine (DICOM) query/retrieve capabilities of a DICOM application implemented on a DICOM device by performing a list of queries to the DICOM application and determining the set of DICOM query/retrieve capabilities based on responses to the list of queries from the DICOM application; populating a DICOM conformance statement with the obtained set of DICOM query/retrieve capabilities; and outputting the DICOM conformance statement for display on a display device. In a first example of the method, the method further includes storing a machine-readable version of the DICOM conformance statement in memory of the computing device. In a second example of the method, which optionally includes the first example, determining the set of DICOM query/retrieve capabilities comprises identifying one or more supported service object pair (SOP) classes related to query/retrieve, and for each supported SOP class, identifying one or more tags of that SOP class. In a third example of the method, which optionally includes one or both of the first and second examples, determining the set of DICOM query/retrieve capabilities comprises determining a respective query level and matching capabilities for each tag of each supported SOP class. In a fourth example of the method, which optionally includes one or more or each of the first through third examples, the matching capabilities comprise whether or not the DICOM application supports universal matching, single value matching, multiple value matching, wild card matching, and/or range value matching.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   determining a set of digital imaging and communications in medicine (DICOM) query/retrieve capabilities of a DICOM application implemented on a DICOM device by performing a list of queries to the DICOM application; and
   populating a DICOM conformance statement with the determined set of DICOM query/retrieve capabilities, wherein determining the set of DICOM query/retrieve capabilities comprises determining whether or not the DICOM application supports universal matching, and wherein determining universal matching capabilities by performing a list of queries to the DICOM application comprises:
      assembling a list of patient IDs associated with exams stored on the DICOM device;
      for each patient ID on the list, sending a universal matching query to the DICOM application, each universal matching query including a selected tag in a return key;
      if at least one response from the DICOM device to a universal matching query includes a return value for the selected tag, indicating that the DICOM application supports universal matching for the selected tag; and
      if each response from the DICOM application to each universal matching query does not include a return value for the selected tag, indicating that the DICOM device does not support universal matching.

2. The method of claim 1, wherein determining the set of DICOM query/retrieve capabilities comprises identifying one or more supported service object pair (SOP) classes related to query/retrieve, and, for each supported SOP class, identifying one or more tags of that SOP class.

3. The method of claim 1, wherein determining the set of DICOM query/retrieve capabilities comprises determining a respective query level and matching capabilities for each of one or more tags identified for each of one or more supported service object pair (SOP) classes related to query/retrieve.

4. The method of claim 1, wherein determining the set of DICOM query/retrieve capabilities comprises determining matching capabilities, and wherein the matching capabilities comprise whether or not the DICOM application supports universal matching, single value matching, multiple value matching, wild card matching, and/or range value matching.

5. The method of claim 1, wherein determining the set of DICOM query/retrieve capabilities comprises determining whether or not the DICOM application supports single value matching, and wherein determining single value matching capabilities by performing a list of queries to the DICOM application comprises:
   performing a pass test that includes, for each response to each universal matching query, a first single value query for a selected tag using a respective return value from that response;
   performing a fail test that includes, for each response to each universal matching query, a second single value query for the selected tag using a different value than the respective return value from that response; and
   if both the pass test and the fail test return expected results, indicating that the DICOM application supports single value matching for the selected tag.

6. The method of claim 1, wherein determining the set of DICOM query/retrieve capabilities comprises determining whether or not the DICOM application supports wild card matching, and wherein determining wild card matching capabilities by performing a list of queries to the DICOM application comprises:
   for each return value from each response to each universal matching query, transforming the last character of the return value for that response to a wild card and performing a wild card query with the transformed return value; and
   if each wild card query returns expected results, indicating that the DICOM application supports wild card matching.

7. The method of claim 1, wherein determining the set of DICOM query/retrieve capabilities comprises determining whether or not the DICOM application supports range value matching, and wherein determining range value matching capabilities by performing a list of queries to the DICOM application comprises:
   selecting a DICOM reference object based on each response to each universal matching query, and identifying the return value of the selected tag for the DICOM reference object;
   performing a first range value query using a first range that spans the return value of the selected tag for the DICOM reference object;
   performing a second range value query using a second range that does not span the return value of the selected tag for the DICOM reference object; and if both the first range value query and the second range value query return expected results, indicating that the DICOM application supports range value matching.

8. The method of claim 1, wherein determining the set of DICOM query/retrieve capabilities comprises determining whether or not the DICOM application supports multiple value matching, and wherein determining multiple value matching capabilities for the selected tag comprises:
selecting a DICOM reference object based on each response to each universal matching query, and identifying the return value of the selected tag for the DICOM reference object;
performing a first multiple value query using the return value of the selected tag for the DICOM reference object and a virtual value, in a first order;
performing a second multiple value query using the return value of the selected tag for the DICOM reference object and the virtual value, in a reversed order relative to the first order;
performing a third multiple value query using two virtual values; and
if the first multiple value query, the second multiple value query, and the third multiple value query each return expected results, indicating that the DICOM application supports multiple value matching.

9. The method of claim 1, further comprising outputting the DICOM conformance statement for display on a display device.

10. The method of claim 1, wherein populating the DICOM conformance statement with the determined set of DICOM query/retrieve capabilities comprises populating a machine-readable DICOM conformance statement with the determined set of DICOM query/retrieve capabilities.

11. A method, comprising:
determining a set of digital imaging and communications in medicine (DICOM) query/retrieve capabilities of a DICOM application implemented on a DICOM device by performing a list of queries to the DICOM application that includes sending a matching capabilities query to the DICOM application;
if a response from the DICOM application comprises an expected value, indicating that the DICOM application supports the matching capabilities query;
if the response from the DICOM application does not comprise the expected value, indicating that the DICOM application does not support the matching capabilities query; and
populating a DICOM conformance statement with the determined set of DICOM query/retrieve capabilities, wherein determining the set of DICOM query/retrieve capabilities comprises determining whether or not the DICOM application supports universal matching, and wherein determining universal matching capabilities by performing a list of queries to the DICOM application comprises:
assembling a list of patient IDs associated with exams stored on the DICOM device;
for each patient ID on the list, sending a universal matching query comprising the matching capabilities query to the DICOM application, each universal matching query including a selected tag in a return key;
if at least one response from the DICOM device to a universal matching query includes a return value for the selected tag, indicating that the DICOM application supports universal matching for the selected tag; and
if each response from the DICOM application to each universal matching query does not include a return value for the selected tag, indicating that the DICOM device does not support universal matching.

12. The method of claim 11, wherein the matching capabilities query includes one or more of a universal matching query, a single value matching query, a multiple value matching query, a wild card matching query, and a range value matching query.

13. The method of claim 11, wherein determining the set of DICOM query/retrieve capabilities comprises determining whether or not the DICOM application supports single value matching, and wherein determining single value matching capabilities by performing a list of queries to the DICOM application comprises:
performing a pass test that includes, for each response to each universal matching query, a first single value query for a selected tag using a respective return value from that response;
performing a fail test that includes, for each response to each universal matching query, a second single value query for the selected tag using a different value than the respective return value from that response; and
if both the pass test and the fail test return expected results, indicating that the DICOM application supports single value matching for the selected tag.

14. The method of claim 11, wherein determining the set of DICOM query/retrieve capabilities comprises determining whether or not the DICOM application supports wild card matching, and wherein determining wild card matching capabilities by performing a list of queries to the DICOM application comprises:
for each return value from each response to each universal matching query, transforming the last character of the return value for that response to a wild card and performing a wild card query with the transformed return value; and
if each wild card query returns expected results, indicating that the DICOM application supports wild card matching.

15. The method of claim 11, wherein determining the set of DICOM query/retrieve capabilities comprises determining whether or not the DICOM application supports range value matching, and wherein determining range value matching capabilities by performing a list of queries to the DICOM application comprises:
selecting a DICOM reference object based on each response to each universal matching query, and identifying the return value of the selected tag for the DICOM reference object;
performing a first range value query using a first range that spans the return value of the selected tag for the DICOM reference object;
performing a second range value query using a second range that does not span the return value of the selected tag for the DICOM reference object; and
if both the first range value query and the second range value query return expected results, indicating that the DICOM application supports range value matching.

16. The method of claim 11, wherein determining the set of DICOM query/retrieve capabilities comprises determining whether or not the DICOM application supports multiple value matching, and wherein determining multiple value matching capabilities for the selected tag comprises:

selecting a DICOM reference object based on each response to each universal matching query, and identifying the return value of the selected tag for the DICOM reference object;

performing a first multiple value query using the return value of the selected tag for the DICOM reference object and a virtual value, in a first order;

performing a second multiple value query using the return value of the selected tag for the DICOM reference object and the virtual value, in a reversed order relative to the first order;

performing a third multiple value query using two virtual values; and if the first multiple value query, the second multiple value query, and the third multiple value query each return expected results, indicating that the DICOM application supports multiple value matching.

17. The method of claim 11, further comprising outputting the DICOM conformance statement for display on a display device.

18. The method of claim 11, wherein populating the DICOM conformance statement with the determined set of DICOM query/retrieve capabilities comprises populating a machine-readable DICOM conformance statement with the determined set of DICOM query/retrieve capabilities.

* * * * *